US007771775B2

(12) United States Patent
Lawrynowicz et al.

(10) Patent No.: US 7,771,775 B2
(45) Date of Patent: Aug. 10, 2010

(54) METHOD FOR FABRICATING A MEDICAL COMPONENT FROM A MATERIAL HAVING A HIGH CARBIDE PHASE

(75) Inventors: Daniel E. Lawrynowicz, Cornwall, NY (US); Aiguo Wang, Wayne, NJ (US); Zongtao Zhang, Unionville, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 448 days.

(21) Appl. No.: 11/728,677

(22) Filed: Mar. 26, 2007

(65) Prior Publication Data

US 2008/0241350 A1 Oct. 2, 2008

(51) Int. Cl.
*A61L 33/00* (2006.01)

(52) U.S. Cl. ........................ 427/2.1; 623/23.55; 623/18; 623/22; 264/81; 156/603; 75/10.13; 427/2.24; 427/2.26; 427/2.27; 427/446; 427/447; 427/448; 427/450; 427/455; 427/456; 427/457; 427/569; 427/576; 427/577; 427/133

(58) Field of Classification Search .................. 623/18, 623/22, 23.55; 75/10.13; 264/81; 156/603, 156/610; 427/446–456
See application file for complete search history.

(56) References Cited

U.S. PATENT DOCUMENTS

| | | | | |
|---|---|---|---|---|
| 2,685,543 | A | | 8/1954 | Sindeband |
| 4,153,453 | A | | 5/1979 | Hart et al. |
| 4,687,487 | A | * | 8/1987 | Hintermann ............. 623/18.11 |
| 5,242,479 | A | * | 9/1993 | Movchan et al. ........... 75/10.13 |
| 5,256,243 | A | * | 10/1993 | Kida ........................... 117/75 |
| 5,370,694 | A | | 12/1994 | Davidson |
| 5,480,438 | A | | 1/1996 | Arima et al. |
| 5,509,933 | A | | 4/1996 | Davidson et al. |
| 5,868,796 | A | | 2/1999 | Buechel et al. |
| 5,954,724 | A | | 9/1999 | Davidson |
| 6,139,585 | A | | 10/2000 | Li |
| 6,187,045 | B1 | | 2/2001 | Fehring et al. |
| 6,312,473 | B1 | | 11/2001 | Oshida |
| 6,425,922 | B1 | | 7/2002 | Pope et al. |
| 6,447,550 | B1 | | 9/2002 | Hunter et al. |
| 6,585,772 | B2 | | 7/2003 | Hunter et al. |
| 6,652,588 | B2 | | 11/2003 | Hayes, Jr. et al. |
| 6,723,177 | B2 | | 4/2004 | Dearnaley et al. |

(Continued)

FOREIGN PATENT DOCUMENTS

JP 360003299 A * 1/1985

*Primary Examiner*—Michael Barr
*Assistant Examiner*—Andrew Bowman
(74) *Attorney, Agent, or Firm*—Lerner, David, Littenberg, Krumholz & Mentlik, LLP

(57) ABSTRACT

A method of fabricating a medical implant component. The method may comprise producing a substrate from a first material in which the substrate has a bearing portion, and spraying particles of a second material by use of a thermal type spraying process onto at least the bearing portion of the substrate. The second material may be formed from a biocompatible material and a carbide source, in which the carbide source is 6.17% or more of the second material by weight. The biocompatible material may be cobalt chrome and the carbide source may be graphite. The thermal type spraying process may be a plasma spraying process or a high velocity oxygen fuel spraying process.

16 Claims, 4 Drawing Sheets

U.S. PATENT DOCUMENTS

| | | | |
|---|---|---|---|
| 6,773,520 | B1 | 8/2004 | Fehring et al. |
| 6,881,229 | B2 | 4/2005 | Khandkar et al. |
| 2002/0038149 | A1 | 3/2002 | Hall et al. |
| 2002/0052659 | A1 | 5/2002 | Hayes et al. |
| 2003/0049485 | A1 | 3/2003 | Brupbacher et al. |
| 2003/0125808 | A1 | 7/2003 | Hunter et al. |
| 2003/0171820 | A1 | 9/2003 | Wilshaw et al. |
| 2003/0220696 | A1 | 11/2003 | Levine et al. |
| 2004/0002766 | A1 | 1/2004 | Hunter et al. |
| 2004/0043230 | A1 | 3/2004 | Hatono et al. |
| 2004/0133283 | A1 | 7/2004 | Shetty |
| 2004/0249469 | A1 | 12/2004 | Cohen et al. |
| 2005/0025896 | A1 | 2/2005 | Grinberg et al. |
| 2005/0026001 | A1 | 2/2005 | Taylor |
| 2005/0107870 | A1 | 5/2005 | Wang et al. |
| 2005/0241736 | A1 | 11/2005 | Bell et al. |

* cited by examiner

METHOD FOR FABRICATING A MEDICAL COMPONENT FROM A MATERIAL HAVING A HIGH CARBIDE PHASE

BACKGROUND OF THE INVENTION

The present invention relates to a method of fabricating a medical component, such as a medical implant, from a biocompatible material having a relatively high concentration of a carbide or carbon source and to such medical component.

Medical components, such as medical implant components, may be formed or fabricated from a material or materials having good wear properties. As an example, such components may be formed or fabricated from a biocompatible material such as cobalt chrome or a cobalt chrome alloy having a carbide content. For medical implants, such carbide content may comprise a relatively small percentage of the final material, such as less than 6.17% by weight thereof and typically only approximately 3-5% by weight thereof.

The carbide content is primarily responsible for the good wear properties of the above-mentioned cobalt chrome alloy. As is to be appreciated, if the percentage of carbide content in a material (such a cobalt chrome alloy) could be increased, then the wear properties of the resultant alloy or material could be improved. However, increasing the carbide content may result in a decrease of other properties. For example, increasing the carbide content in a biocompatible material (such as cobalt chrome) may reduce the fatigue life, strength, corrosion resistance, and toughness, may produce a material which is relatively highly brittle, and/or may reduce the uniformity of the material and produce a material which is relatively highly non-uniform.

The decrease in the above-identified properties (especially the uniformity) may make the resultant material difficult to machine. More specifically, if the carbide content is increased beyond a certain amount, the carbide content in the biocompatible material may not completely mix with the biocompatible material. As a result, the biocompatible material may have some of the carbide constituent or particles completely mixed therein and may have some of the carbide particles which are not completely mixed or not at all mixed therein. Such situation may be considered similar to that of adding sugar to a glass of water. In this later situation, after a certain amount of sugar is added, the sugar no longer mixes or dissolves in the water. Instead, some of the sugar remains in a non-dissolved or a not completely dissolved state.

To further describe the above-mentioned machining difficulty of a material having an increased carbide content, consider the parts illustrated in FIGS. 3A and 3B. With reference to FIG. 3A, unmixed carbide particles 90 contained within an item 92 formed from biocompatible material and carbide may be relatively large, such as between 5-20 microns in size or length. Additionally, the carbide particles 90 may be relatively strong. As a result, machining or cutting such material properly may be difficult if not impossible. For example, and with reference to FIG. 3B, if a surface 94 of the item 92 to be machined contains a number of relatively large carbide particles 90, then during a machining operation thereof when a cutting tool 96 encounters a portion 98 of a respective carbide particle 90, instead of just the desired portion of such carbide particle being cut, the entire particle may be removed thereby leaving a depression in the surface. As such, it may be very difficult, if not impossible, to properly machine surface 94 (having the relatively large size carbide particles 90) to a desired thickness or dimension T. In other words, even if the item 92 is actually machined so as to have thickness/dimension T, the machined surface may contain a number of depressions or voids and, as such, may not have a desired surface roughness or finish. Additionally, since the carbide particles 90 are relatively strong, the cutting tool 96 may be damaged during the machining or cutting operation.

A description of a material which may be typically used for medical implant components will now be provided.

A material typically used in the fabrication of medical implant components is ASTM F75, ISO 5832, where CoCrMo alloy composing of 1-5 vol % carbides with atomic composition by weight percent of C 0.28-0.35, Cr 28.10-28.31, Mo 5.61-5.92, Si 0.95-0.96, Mn 0.36-0.40, Ni 0.27-0.73, Fe 0.14-0.24, W 0.04-0.05, Co balance, and other elements<0.001. The carbide phases are M23C6, M7C3, M3C2, and MC, where M is metallic elements of Cr, Mo, W. The primary phase is Cr23C6. Usually, as cast CoCrMo may have a carbide content of about 5% in volume. Merely increasing the carbide content in as-cast CoCrMo alloy may result in a decrease of corrosion resistance, strength, toughness, and fatigue life due to the inability of all of the carbide particles to go into solution and the tendency to precipitate at the grain boundary during solidification.

Additionally, another limitation associated with the use of the F75 CoCrMo alloy may be due to the large size of the carbide particles. As indicated by Cawley et al., the size of the carbide particles in F75 may be larger than 1.0 micron (1000 nm) and may be within the range of 10-100 μm. According to the Hall-Petch relationship, the hardness is inversely proportional to the square root of carbide size in alloys. In other words, the larger the size, the lower the hardness and, additionally the lower the strength and toughness.

Accordingly, it has been very difficult, if not impossible, to fabricate a medical implant or component from a biocompatible material having a relatively high carbide content, such as that of 6.17% by weight or higher.

It would be advantageous to provide a technique for fabricating a medical component, such as a medical implant, from a biocompatible material or alloy having a relatively high carbon or carbide content so as to increase the wear properties over that obtained from currently used biocompatible materials. It would be further advantageous to provide such technique whereby the biocompatible material or alloy would have relatively good fatigue properties, would not be highly brittle, and would be relatively uniform or homogeneous.

SUMMARY OF THE INVENTION

In accordance with an aspect of the present invention, a method of fabricating a medical implant component is provided. The method may comprise producing a substrate from a first material in which the substrate has a bearing portion, and spraying particles of a second material by use of a thermal type spraying process onto at least the bearing portion of the substrate. The second material may be formed from a biocompatible material and a carbide source, in which the carbide source is 6.17% or more of the second material by weight.

In accordance with another aspect of the present invention, a method of fabricating a medical implant component is provided. The method may comprise producing a sacrificial substrate representative of the medical implant component from a first material; spraying particles of a second material by use of a thermal type spraying process onto the sacrificial substrate, in which the second material may be formed from a biocompatible material and a carbide source, and in which the carbide source is 6.17% or more of the second material by weight; and removing the sacrificial substrate.

The biocompatible material may be cobalt chrome and the carbide source may be graphite. Additionally, the thermal type spraying process may be a plasma spraying process or a high velocity oxygen fuel spraying process.

DETAILED DESCRIPTION

A technique for fabricating or forming a medical component (such as a medical implant device) using a biocompatible material or alloy having a relatively high concentration of a carbon or carbide constituent will now be described. Initially, a description will be provided pertaining to a number of methods for producing a biocompatible material or alloy having a relatively high concentration of a carbon or carbide constituent. With regard thereto, U.S. patent application Ser. No. 11/728,678 filed Mar. 26, 2007, entitled "Method for Fabricating a Biocompatible Material having a High Carbide Phase and Such Material" with inventors Daniel E. Lawrynowicz, Aiguo Wang, and Zongtao Zhang, is hereby incorporated by reference.

As hereinafter more fully described, the carbide concentration or the amount of carbide may be 6.17 percent or higher of the total weight of the formed biocompatible material. In fact, such carbide content may have any value from 6.17 percent and up, such as 25%, 50%, 75% or higher of the total weight of the formed biocompatible material. Such formed biocompatible material may be used in the fabrication of medical implant components. For example, such material may be utilized to form a medical implant component or to coat one or more surfaces of a medical implant component, such as an acetabular cup, a femoral head, a femoral knee, a tibial knee, a shoulder component, or a spine component by use of a spraying operation, as herein below more fully described.

A system 10 which may be utilized to fabricate or form a biocompatible material or alloy having a relatively high concentration of a carbon or carbide constituent will now be described with reference to FIGS. 1, 2A, and 2B. In general, the system 10 may be utilized to combine a biocompatible material or alloy with a carbon or carbide source so as to obtain the desired material. The biocompatible material or alloy may be one of cobalt chrome, titanium (Ti), a titanium alloy, zirconium (Zr), a zirconium alloy, stainless steel, a cobalt based super alloy, and so forth; and the carbon or carbide source may be one of graphite, coke, pitch, diamond, diamond dust and so forth.

Figure 1:
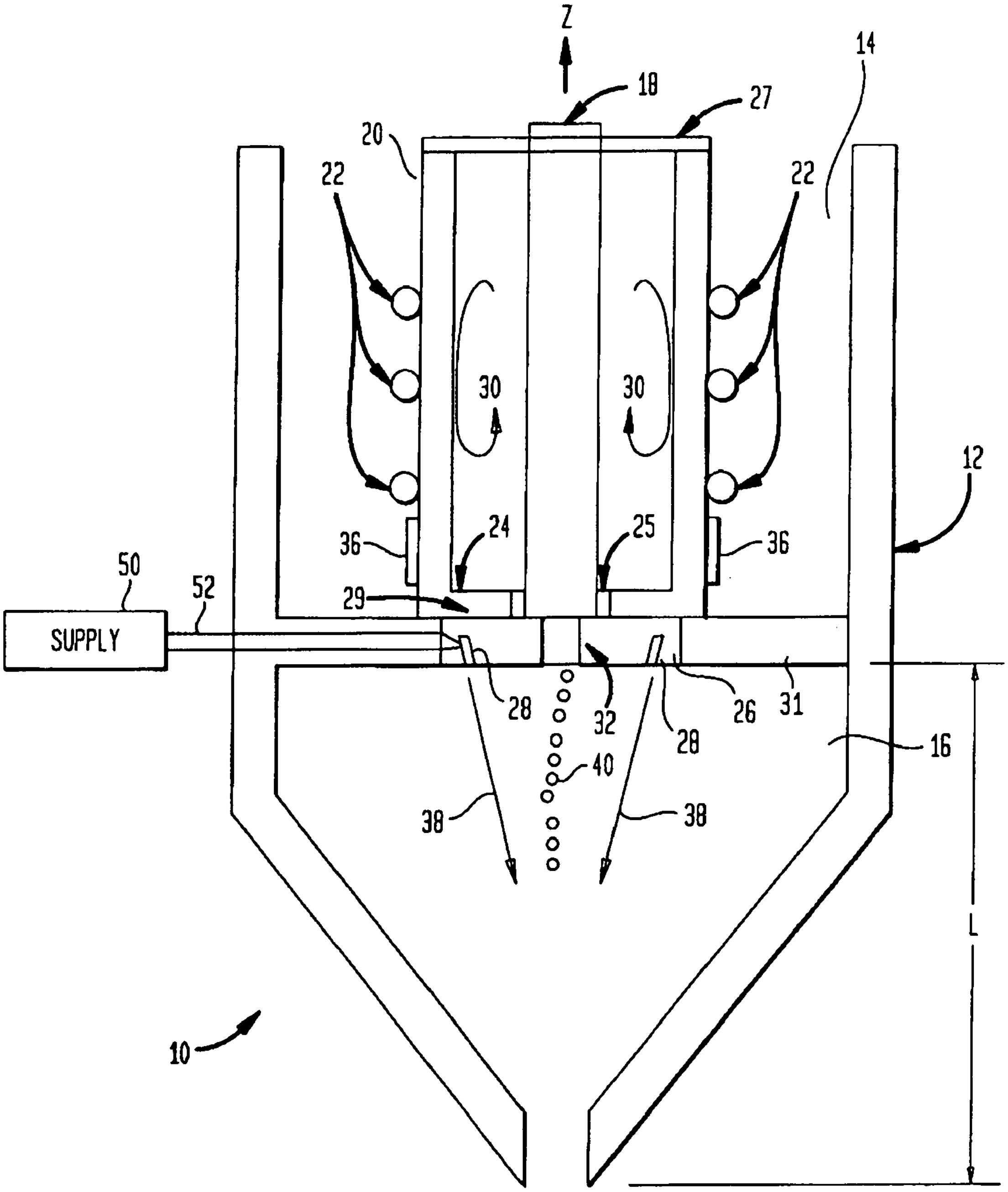
FIG. 1 is a cross-sectional diagram of a system to which reference will be made in explaining a method for producing a material having a relatively high carbide content.

FIG. 1 illustrates a cross-sectional diagram of system or apparatus 10. As shown therein, system or apparatus 10 may generally include a vessel or container 12, a container or crucible 20, a stopper rod 18, and an atomizer 26.

The vessel 12 may have a first portion 14 and a second portion 16. The vessel 12 may be fabricated from a metal or other type material. The vessel may be configured such that the first portion 14 is large enough to hold the crucible 20 and such that the second portion 16 is sufficiently large to enable an atomization process to be properly performed, as herein below more fully described. With regard to the second portion 16, the length L thereof may have a value in the range of approximately 2 feet to 10 feet.

The crucible 20 may be fabricated from a ceramic or other non-metal material and may have a generally cylindrical shape. The crucible 20 may have a base portion 24 located at the bottom thereof. A hole 25 may be located in the center of the base portion 24 and may be sized or configured so as to allow the rod 18 to pass therethrough and sit on the atomizer 26. The crucible 20 may be adapted to receive a number of materials which are to be combined. Such materials may include a biocompatible material or alloy (such as cobalt chrome) and a carbon or carbide source (such as graphite). A top portion 27 may be placed on top of the crucible 20 so that during operation the crucible may be substantially closed.

Figure 2A:
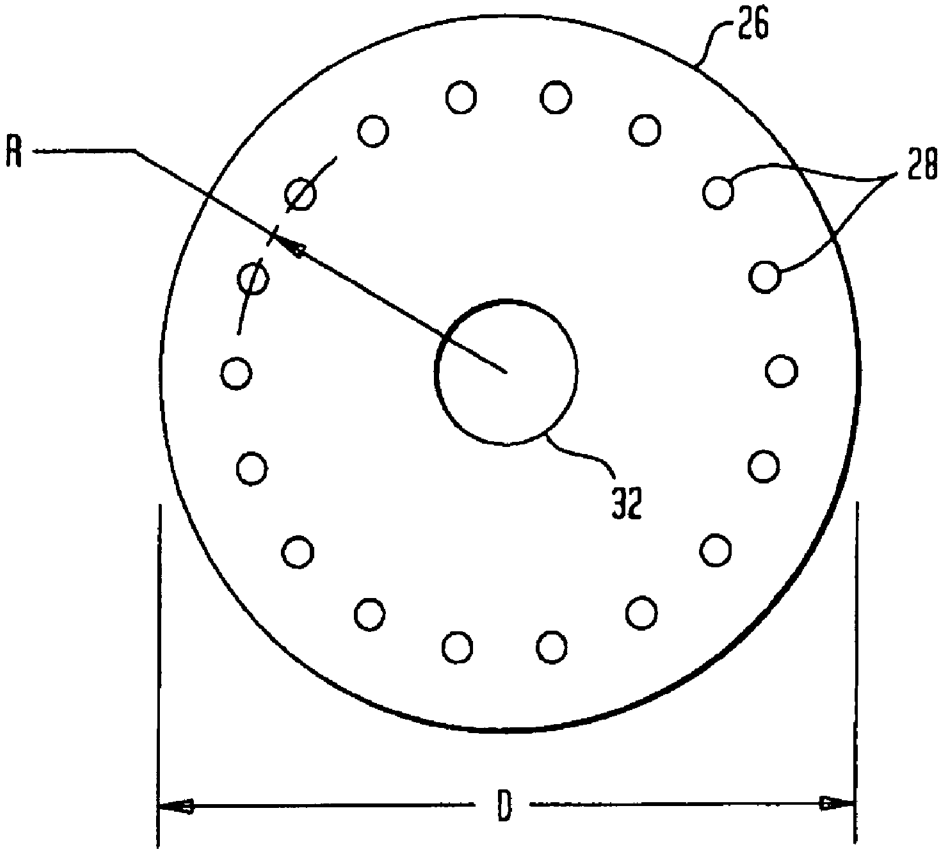
FIGS. 2A and 2B are diagrams of a top view and a side view, respectively, of a base plate which may be used in the system of FIG. 1.
Figure 2B:
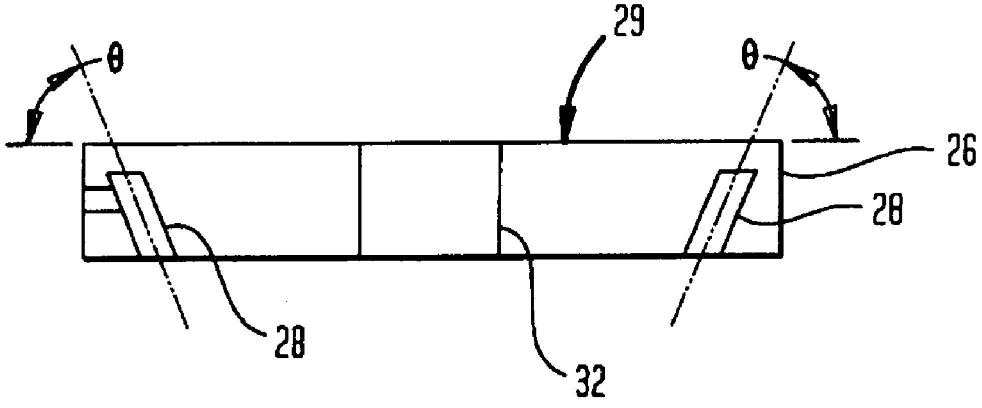

With reference to FIG. 1 and FIG. 2A, the atomizer 26 may be arranged within a center portion of a member 31 of the vessel 12. The atomizer 26 may have a generally disc shape and may have an outer dimension or diameter D which is larger than that of the rod 18. The atomizer 26 may include a through hole 32 located in the center thereof. Such hole 32 may have a size or diameter in the range of approximately 0.125 to 0.5 inches. Additionally, the atomizer 26 may include a plurality of holes 28 each located at a distance R from the center of the atomizer and near the periphery thereof. As best shown in FIG. 2B, each of the holes 28 may be inclined, that is, positioned at a predetermined angle Ø with regard to an outer surface 29 of the atomizer 26. Such predetermined angle Ø may have a value in the range of approximately 20 degrees to 70 degrees.

Each of the holes 28 may be coupled to a fluid supply 50 by way of a connection within the atomizer 26 and/or a hose 52 or other type of connection. The fluid supply 50 may contain a predetermined gas or liquid. As an example, such predetermined gas may be argon or nitrogen, and such predetermined liquid may be water. Additionally, the gas may be reactive with the biocompatible material. For example, the biocompatible material may be cobalt chrome and the gas may be methane or a blend having methane. The fluid may be contained within the supply 50 under a relatively high pressure, such as 60-300 pounds per square inch (psi).

The stopper rod 18 may have a generally cylindrical shape and may be configured so as to be movable within the crucible 20 along a Z direction between a first position in which the stopper rod is located on surface 29 of the atomizer 26 and a second position in which the stopper rod is located above the surface 29. More specifically, the stopper rod 18 may have a diameter which is smaller than that of hole 25 of the crucible 20 as previously indicated and larger than that of the hole 32 of the atomizer 26. As a result, when the stopper rod 18 is positioned in its first position, the stopper rod may be arranged on top of the hole 32 and may cover hole 32 so as to prevent material from passing from inside the crucible 20 to the second portion 16 of the vessel 12. And, when the stopper rod 18 is arranged in its second position, the stopper rod will not cover hole 32 so as to enable material to pass from inside the crucible 20 to the second portion 16 of the vessel 12.

A number of induction coils 22 may be arranged around the crucible 20. More specifically, such induction coils 22 may be arranged in a spiral manner around the outside and/or inside of the container 20. The induction coils 22 may be tubes fabricated from a predetermined material, such as copper, having a fluid such as water inside thereof. An electric current having a predetermined value, such as approximately 6000 amperes (amps), may be applied to the induction coils 22. Applying such current or power to the induction coils 22 may cause the material contained within the crucible 20 to be moved or stirred in a predetermined direction, such as in an up/down direction as indicated by arrows 30. Additionally, when activated, such induction coils 22 may apply heat to the crucible 20 so as to cause the materials contained therein to be heated to a predetermined temperature. As an example, such predetermined temperature may be approximately 200 to 300 degrees Centigrade over the melting point of at least one material contained in the crucible 20. As a result, and during operation, the materials contained within the crucible 20 may be stirred/mixed together and may be heated to a predetermined temperature.

Additionally, one or more heaters 36 may also be arranged on and/or in the crucible 20. Such heater or heaters 36 may be operable to apply heat to the crucible 20 to cause the materials contained therein to be heated. The heaters 36 may be utilized to supplement the heat provided by use of the induction coils 22. Alternatively, the heaters 36 may be utilized as the primary source of heat. As an example, consider the situation wherein the induction coils 22 are not used and instead another device is utilized to stir the materials in the crucible 20. In such situation, if the other device does not provide heat or does not provide sufficient heat, then the heaters 36 may be utilized.

During operation, the rod 18 may be placed in its first position so that the hole 32 in the atomizer 26 is covered. Thereafter, a desired biocompatible material (such as cobalt chrome) and a desired carbon or carbide source (such as graphite) may be added to the crucible 20. The amounts of the cobalt chrome and carbon or carbide source which are added may be dependent upon the desired amount of carbon or carbide in the final material. For example, if the resultant desired material is to be a cobalt chrome alloy having a 75 percent carbide phase or content, then one part cobalt chrome would be added for each three parts of carbide. This ratio of 1:3 may be by weight or volume. After the desired amounts of cobalt chrome and carbide are added to the crucible 20, current (such as 6000 amps) may be applied to the induction coils 22 so as to cause the materials contained within the crucible 20 to be stirred or mixed in the up/down directions as indicated by the arrows 30, and heated to a predetermined temperature such as 200 to 300 degrees over the melting point of the one of the materials contained in the crucible 20 which has the lower melting point temperature (which, as an example, may be the cobalt chrome). Additionally, the heater(s) 36 may be activated so as to supplement the heating of the materials (cobalt chrome and carbide) in the crucible 20. At the predetermined temperature (which may be the lower melting point temperature of the two melting point temperatures associated with the materials inside the crucible 20), the material in the crucible 20 which has the higher melting point temperature may dissolve or go into solution. Such material may then be in a solid diffusion state.

Thus, the induction coils 22 and/or the heaters 36 may be activated for a sufficient time so as to enable the materials contained within the crucible 20 to be properly mixed together and heated to the predetermined temperature. As a result, the biocompatible material or alloy (such as cobalt chrome) may be melted and the carbide source may be allowed to go into solution so as to form a molten homogeneous solution.

Thereafter, the stopper rod 18 may be moved along the Z direction from its first position to its second position so as to uncover the hole 32 in the atomizer 26. As a result, the molten homogeneous solution from the crucible 20 may pass through the hole 32 in the atomizer 26 and into the second portion 16 of the vessel 12. At the same time or prior to such time, the high pressure fluid (which may be a gas such as argon or nitrogen or which may be a liquid such as water) from the supply 50 may be supplied by way of hoses 52 to the inclined holes 28 in the atomizer 26. As a result, a high pressure gas or liquid may be supplied into the portion 16 in a direction as indicated by arrows 38 while particles 40 of the molten homogeneous solution from the crucible 20 are supplied into the portion 16 as indicated in FIG. 1. Such directed high pressure gas or liquid may impinge the particles 40 of the molten homogeneous solution so as to form spray atomized powder of a final material which, in the current example, may be a cobalt chrome alloy having a 75 percent carbide phase.

Figure 3A:
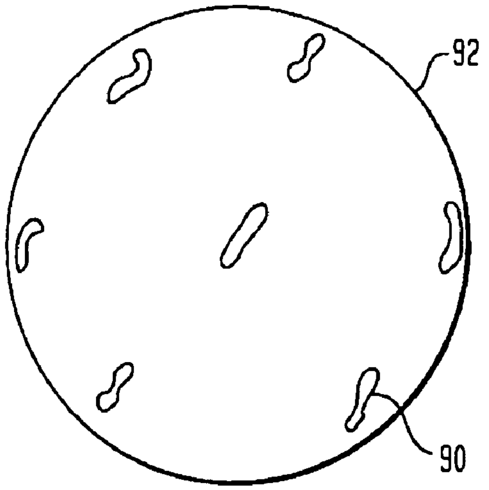
FIGS. 3A and 3B are diagrams of a top view and a side view, respectively, of an item to which reference will be made in explaining a disadvantage of a material with relatively large size carbide particles.
Figure 3B:
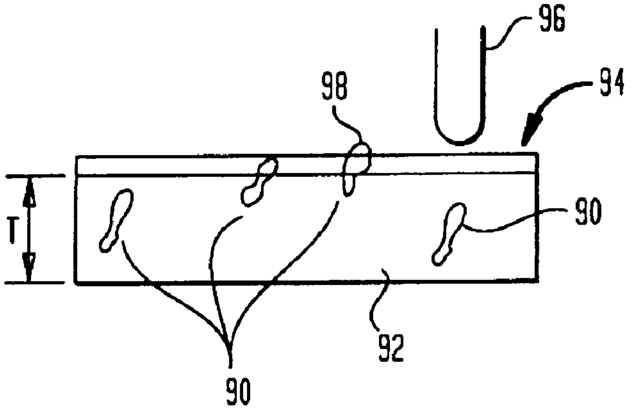
Figure 3C:
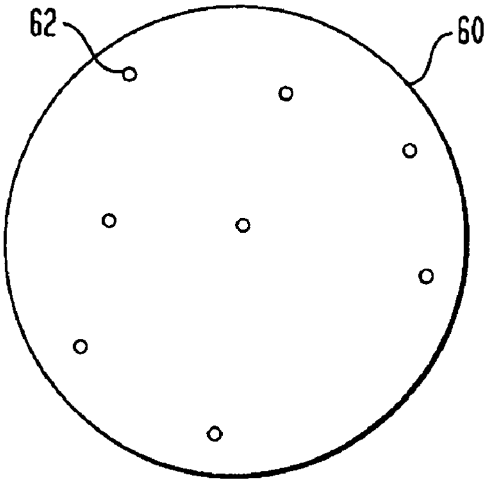
FIG. 3C is a diagram to which reference will be made in describing a item having a relatively high carbide content produced by use of the system of FIG. 1.

The final produced material (i.e., the cobalt chrome alloy having a 75 percent carbide phase) may contain carbide particles which are substantially smaller than those previously described with reference to FIGS. 3A and 3B. As an example, and with reference to FIG. 3C, the size of carbide particles 62 contained within an item or medical component 60 formed from the final produced material may have a value less than approximately nine hundred (900) nanometers and may preferably be within the range of approximately 40-200 nanometers. As is to be appreciated, even though the carbide particles are relatively strong, since the size of the carbide particles 62 is relatively small, a machining operation of a surface of item 60 may not have the difficulties previously described with regard to an item having relatively large size carbide particles (such as that described with reference to FIGS. 3A and 3B).

Thus, the system 10 enables a biocompatible material (such as a cobalt chrome alloy) to be formed which has a carbide content or phase of 75 percent.

Although in the above example, a carbide content of 75 percent was produced, system 10 is not so limited. In fact, the system 10 may be utilized to obtain a biocompatible material with a carbide or carbon content having other values, such as a carbide content of 6.17 percent or higher up to nearly 100 percent. As an example, the system 10 may be utilized to obtain a biocompatible material with a carbide content of 10, 25, 50, 70, or even higher of the total weight of the formed material.

Alternatively, a carbon or carbide source in a powder form may be added to a desired biocompatible material in a powder form and mixed together so as to form a powder mixture thereof. Particles of the powdered carbon or carbide source may have a size within a predetermined range and particles of the powdered biocompatible material may have a size within a predetermined range. By adding a desired amount of the carbon or carbide source to a given amount of the biocompatible material, the resultant powder mixture may have the desired amount of carbon or carbide. Accordingly, such procedure may produce a biocompatible material having a relatively high concentration of a carbon or carbide constituent. Further, since the size of the particles of the powdered carbon or carbide source is relatively small, the obtained mixture may contain only very small sized particles of the carbon or carbide source. As a result, items or medical components or implants formed from the obtained mixture may be easily machined in a manner similar to that previously described with regard to FIG. 3C. The amount or percent of carbon or carbide may have any of a number of values. For example, the carbide content may have any value from 6.17 percent up to nearly 100 percent (such as 10, 15, 25, 50, 75 percent or higher) of the total mixture by weight. Additionally, the biocompatible material or alloy may be cobalt chrome, titanium (Ti), a titanium alloy, zirconium (Zr), a zirconium alloy, stainless steel, or a cobalt based super alloy; and the carbon or carbide source may be graphite, coke, pitch, diamond, or diamond dust. As is to be appreciated, if a final material having a 100 percent of carbon or carbide is desired, such final material would only or substantially only contain the carbon or carbide and would not contain any biocompatible material such as cobalt chrome.

Although several methods have been described herein for producing material having a relatively high carbon or carbide content, the present invention is not so limited. That is, various other methods may be utilized. As an example, powder metallurgy techniques may also be utilized to produce such material. Examples of such powder metallurgy techniques may include a low intensity mechanical blending method in which the biocompatible material and the carbide source are blended together by use of a V-blender, a shaker blender, or similar type device; a mechanical alloying method in which the biocompatible material and the carbide source are blended together by using metal balls; a cryogenic milling method which is similar to the mechanical alloying method except performed under cryogenic conditions at a liquid nitrogen or liquid helium temperature; a fused and crush powder method in which the biocompatible material and the carbide source are mechanically blended, then the powder is fused by use of a furnace (wherein the powder is fused but not sintered), and then crushed to a desired size; or a powder cladding method in which a first or core material (e.g., cobalt chrome) is arranged over a second material (e.g., carbide).

In a cryogenic milling method or a mechanical alloying method, the size of the carbide particles which are started with could have a relatively large size, such as 1 millimeter or more. As a result of either method, the carbide particles may be refined so as to end up with nano-size particles. With regard to the mechanical alloying method, the size of the metal balls, the number of the metal balls, the material of the metal balls, the speed, and the volume of the container used may all affect the size of the carbide particles. Also, in a cryogenic milling method, the particles of the biocompatible metal (along with the carbide) may be refined so as to end up with nano-size particles. However, in a mechanical alloying method, the particles of the biocompatible metal may not be refined to nano-size particles.

In a low intensity mechanical blending method, the size of the carbide particles which are started with may be nano-size particles. In a fused and crush powder method, the size of the carbide particles which are started with may be nano-size particles; however, such starting particle size may be larger (such as 5-250 microns).

In a powder cladding method, nano-size carbide particles may be started with and they may be cladded with metal in a chemical vapor deposition (CVD) process. Alternatively, nano-size metal particles may be started with and they may be cladded with carbide particles which are also nano-sized (CVD process).

Accordingly, as described above, the particles of carbide used to produce a material having a relatively high carbon or carbide content may either start as nano-sized particles or after processing end up as nano-sized particles. Such size may be within the range of less than approximately 900 nanometers and may preferably be within the range of approximately 10-200 nanometers, although the size thereof may be smaller or larger. Additionally, the size of a particle of the biocompatible material in powder form may be approximately 2-300 microns. Further, during the processing, nano-size carbide particles may be clustered together with the particles of the biocompatible material to form a number of agglomerate particles each having a size in the range of approximately 2-300 microns, although such size may be larger or smaller.

The material having a relatively high carbon or carbide content (which may be obtained as described above) may be utilized to form or may be utilized in the fabrication of a medical component or implant as herein below described.

A number of processes may be utilized to form or in the formation of a medical component (such as a medical implant) from the above described high carbon or carbide material. For example, such processes may include any one of a number of spraying techniques, an injection molding technique, a cold isostatic press technique, or a press powder processing technique.

A spraying technique may be utilized to spray material having a relatively high carbon or carbide content onto a desired surface of a substrate of a medical implant. The sprayed material may form a coating having a desired thickness on the desired surface of the substrate. Such spraying technique may be any of a number of spraying techniques such as a thermal spray technique or a so-called high velocity cold spraying process.

The thermal spray technique may be any type of thermal spray technique such as a plasma spraying process or a high velocity oxygen fuel (HVOF) spraying process. The HVOF spraying process may be a gas fuel process such as a propane type process or, alternatively, may be a liquid fuel process such as a kerosene type process.

The high velocity cold spraying process may be that described in co-pending application entitled "High velocity Spray Technique for Medical Implant Components" with inventors Daniel E. Lawrynowicz, Aiguo Wang, and Eric Jones and having Ser. No. 11/325,790, filed Jan. 5, 2006, which is hereby incorporated by reference. Additionally, U.S. application Ser. No. 11/325,841, filed Jan. 5, 2006 entitled "Method for Fabricating a Medical Implant Component and Such Component" with inventors Daniel E. Lawrynowicz and Aiguo Wang and U.S. application Ser. No. 11/325,791 filed Jan. 5, 2006 entitled "Method for Fabricating a Medical Implant Component and Such Component" with inventors Daniel E. Lawrynowicz, Aiguo Wang and Zongtao Zhang which describe spraying techniques for use with medical implants and, in particular, thermal spraying techniques involving hot isostatic pressing, vacuum sintering and controlled atmospheric sintering processes, are both hereby incorporated by reference.

Figure 4:
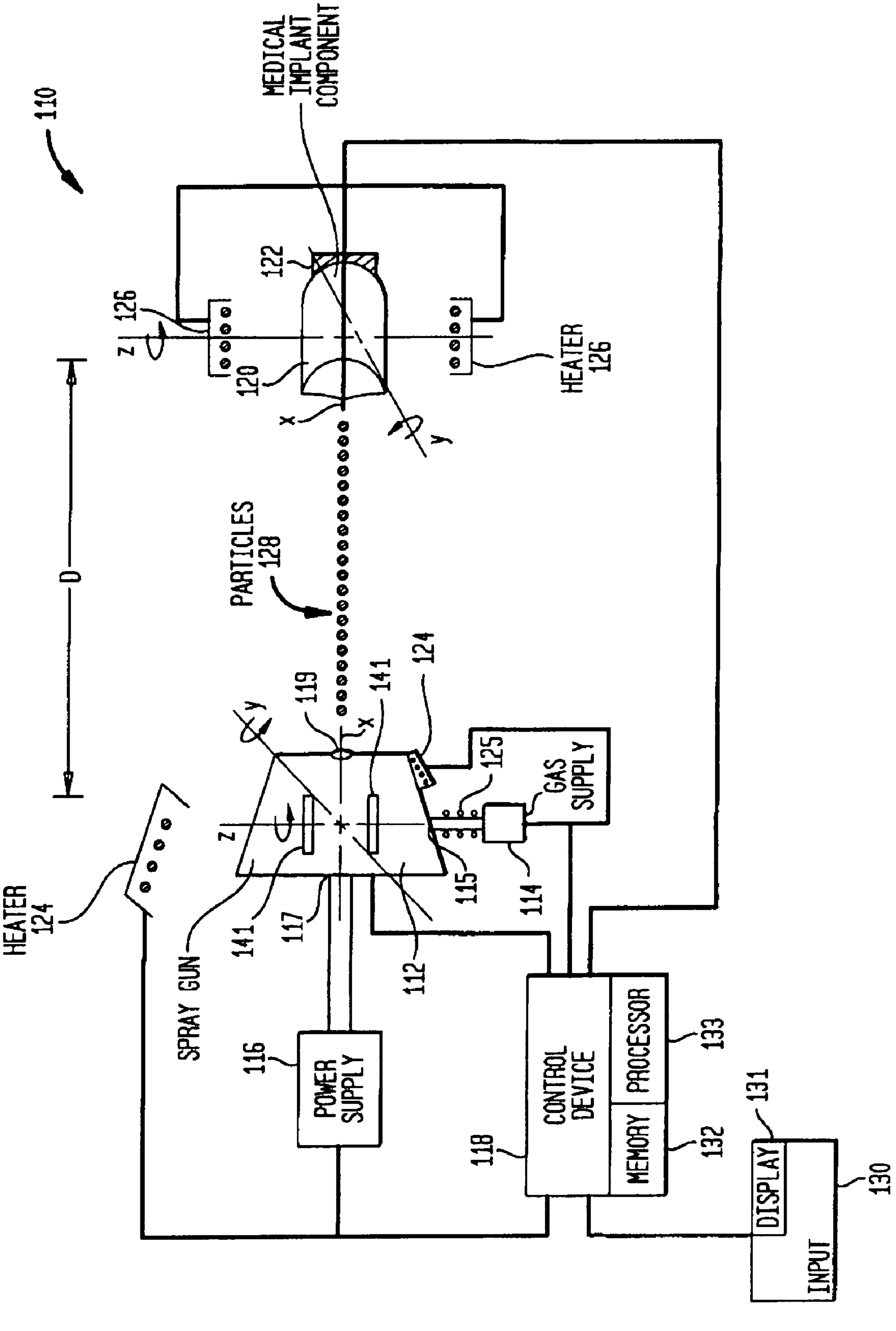
FIG. 4 is a diagram of a spray system which may utilize the material produced from the system of FIG. 1 in accordance with an embodiment of the present invention.

An example of a spray system which may be utilized in performing a spray operation (such as one of the above mentioned spraying processes) is illustrated in FIG. 4. As shown therein, such system may generally include a spray nozzle or gun 112, a control device 118, and a holding fixture 122. The spray gun 112 may include two inlets, a gas inlet 115 and a powder feed inlet 117. The gas inlet 115 may be adapted to receive a gas from a gas supply 114 under relatively high pressure. Such gas may be a low density gas such as helium which may enable higher gas velocities as compared to lower density gases. The powder feed inlet 117 may be adapted to receive the material to be sprayed in a powder or small particle form from a powder supply 116 under relatively high pressure. The spray gun 112 may include one or more internal chambers for receiving the gas and the spray material and for directing the spray material toward an outlet 119 from which the powder or particles 128 may be supplied. Additionally, the chamber or chambers may be configured so as to accelerate the material. As a result, the powder or particles 128 may be supplied or propelled from the outlet 119 at a predetermined relatively high velocity. Such predetermined velocity may have a value in the range between approximately 200 meters/second and up to but not over sonic velocity. Alternatively, the predetermined velocity may be equal to sonic velocity and/or may be over sonic velocity so as to be at supersonic velocity. The actual predetermined velocity may be determined based on the density and/or mass of the spray material.

A component, such as a medical implant component 120, may be positioned or held in place by the holding fixture 122. The medical implant component 120 may, for example, be any one of a femoral knee component, a tibial tray, a patella button, a femoral stem, a femoral head, an acerabular cup, a glenoid/humeral component, or a spinal implant. As is to be appreciated, the medical implant component 120 may be generally arranged such that the surface of the medical implant component to be sprayed faces the spray gun 112. Such spray surface may be a so-called bearing surface, that is, a surface operable to engage or mate with a corresponding surface in another or mating component or with a bone, cartilage and so forth of a patient. Additionally, the holding fixture 122 may be positioned within the system 110 such that the medical implant component 120 (when held by the holding fixture) is positioned at a distance D from the spray gun 112. Such distance D may have a value of approximately 1 to 4 inches.

One or both of the spray gun 112 and the holding fixture 122 may be operable to move and/or rotate. For example, the spray gun 112 may be operable to rotate about one or both of the Y and Z axes, and/or the holding fixture 122 with the medical implant component 120 held therein may be operable to rotate about one or more of the X, Y and Z axes as illustrated in FIG. 4. Additionally, the spray gun 112 and/or the holding fixture 122 (with the medical implant component 120 held therein) may be operable to move in a direction along any one or ones of the X-axis (i.e., toward or away from each other), the Y-axis, and/or the Z-axis.

As a result of the above-described rotation and/or movement, the stream of particles 128 may be moved relative to the component 120. Accordingly, the spray gun 112 may be able to spray particles 128 at the entire desired surface or portion of the medical implant component 120 during a spray operation.

The gas utilized in the spraying process, and/or the powder or particles 128 to be sprayed, and/or the medical implant component 120 may be heated during the spray operation. In this regard, heaters 125 may be arranged on or near the gas supply 114 or the exit thereof so as to cause the gas to be heated, heaters 124 may be arranged on or adjacent to the spray gun 112 so as to cause the powder or particles 128 to be heated, and heaters 126 may be arranged on or adjacent to the fixture 122 and/or the medical implant component 120 so as to cause such component to be heated. Additionally, the particles 128 may be electrically charged by use of a charging device 141. Such charging device 141 may be located within the spray gun 112 and may be adapted to impart an electrical charge to the particles as they pass by.

The control device 118 may include a memory 132 and a processor 133. The memory 132 may have stored therein a number of programs or algorithms usable to operate the system 110. Such programs or algorithms may be operating programs for running the system 110 and/or may include look-up tables or the like usable for generating control signals. The processor 133 may be operable to generate a control signal or signals and to supply such signal(s) to the appropriate one or ones of the devices within the system 110.

The control device 118 may be coupled to an input 130. Such input 130 may include a keyboard type unit and may also include or may be coupled to a display 131. The input unit 130 may be operable to enable an operator to enter a desired command and/or operational information. The control device 118 may be further coupled to a number of or all of the devices in the system 110. Such connection(s) may be provided by a wire, cable, data bus, or the like coupled between the control device 118 and the device(s) of the system 110. Alternatively, such connection(s) may be provided by a wireless means.

As previously indicated, the processor 133 of the control device 118 may be operable to generate one or more control signals and to supply the same to the appropriate one or ones of the devices. More specifically, the control device 118 may be coupled to one or more of the spray gun 112, the gas supply 114, the powder supply 116, the holding fixture 122, the heater 124, the heater 125, and the heater 126; and may be operable to generate and supply control signals thereto so as to control the operation of the same. That is, in response to an input or command from an operator by way of input 130, the processor 133 of the control device 118 may generate an appropriate control signal or signals and cause the same to be supplied to the respective one or ones of the devices of the system 110. For example, in response to an input command from the operator to initiate a spray operation, the control device 118 may generate a gas supply signal and may supply the same to the gas supply 114 so as to control the supply of gas therefrom, and may generate a particle or powder supply signal and may supply the same to the powder supply 116 so as to control the supply of powder therefrom. Such control signals may control the amount of particles 128 supplied from the spray gun 112 and the velocity at which such particles are supplied therefrom. Additionally, the control device 118 may generate movement and/or rotational control signals and may supply the same to the appropriate one or ones of the spray gun 112 and/or the holding fixture 122. Such movement and/or rotational control signals may cause the spray gun 112 and/or the holding fixture 122 (with the medical implant component 120) to be moved/rotated accordingly during the spray operation. Furthermore, if requested by the operator or if appropriate, the control device 118 may generate heating control signals and may supply the same to the appropriate one or ones of the heaters 124, 125, and/or 126. Such heating control signals may cause the heaters 124, 125, and/or 126 to be activated, set to a desired temperature(s), and/or maintained thereat for a predetermined or specified time interval. As a result thereof, the particles 128 and/or the medical implant component 120 may be pre-heated to a desired temperature or temperatures. Additionally, the processor 133 may be operable to receive a feed back type signal or signals regarding the operation of any one or ones of the devices and to use the information therefrom to adjust the appropriate control signal(s).

The spraying process may be controlled or regulated such that a predetermined amount of coating material (i.e., the material having a relatively high carbon or carbide content) is applied to the substrate during a predetermined time interval or during each pass. More specifically, the spraying operation may be performed in an apparatus having a fixture for holding the medical implant component and a spray gun or nozzle from which the coating or spray material is supplied. During the spraying operation, either or both of the spray gun 112 and/or fixture 122 may move in a predetermined or controlled manner. For example, the fixture having the medical implant component 120 may rotate at a predetermined rate in front of the spray gun 112. As a result, the amount of coating material which is applied to the substrate of the medical implant component during each revolution or pass may be controlled to a predetermined value. For example, such control may result in a thickness of coating material of approximately 10 to 12.5 microns or less being applied in each pass. The spraying operation may enable a coating to be applied to a desired surface (such as a bearing portion) of a component with a thickness of 100 to 500 microns, or even thicker. The coating material may be same as that of the substrate, or alternatively, such coating material may be different from the material of the substrate.

After the coating material is applied, it may be subjected to a predetermined thermal consolidation or heat treating process. Such process may be utilized to heat treat the component and/or to create an inter-diffusion region between the coating and the substrate. Examples of such process may include a so-called hot isostatic pressing (HIPing) process, a so-called vacuum sintering process, or a so-called controlled atmospheric sintering process, which may be performed in a control chamber.

Hot isostatic pressing (HIPing) may be performed at relatively high temperatures and/or pressures using a gas such as argon or helium. During such HIPing process, the temperature and the pressure may vary over time in a predetermined manner. Pressureless or vacuum sintering may be performed under a vacuum or at a relatively low pressure or pressures. The pressure may be maintained at a constant or substantially constant value. Such pressure value may be relatively low, such as approximately $10^{-5}$ Torr. Controlled atmospheric sintering may be performed using a noble (or inert) gas, a reactive gas, or a mixture thereof. Examples of such gases may include argon, hydrogen, propane, krypton, carbon dioxide, carbon monoxide, and so forth. Additionally, the gas used in this process may consist entirely or substantially entirely of one of these gases or a blend which includes one of these gases. Furthermore, controlled atmospheric sintering may be performed in a controlled atmospheric setting, such as that created by using a partial pressure of a gas (such as argon). This process may also be considered a positive pressure controlled atmospheric sintering process. A vacuum (or a relatively low pressure) may be maintained for a portion of the process, and then an inert gas (such as argon) may be added so that the pressure may be increased. The vacuum may have a relatively low pressure, such as approximately $10^{-4}$ or $10^{-5}$ Torr, and the pressure may have a low value which may be slightly higher, such as approximately $10^{-3}$ Torr. Argon may be backfilled into the chamber so that the entire chamber or substantially the entire chamber is filled with argon such that the pressure is equal to atmospheric pressure or above.

In addition to utilizing the above-described spray techniques for applying a coating of a material having a relatively high carbon or carbide content onto a surface of a medical implant component; spray techniques may be utilized to form a medical implant. As an example, a so-called sacrificial substrate representative of the medical implant component may be formed from salt or another material which may be easily dissolved, melted or removed. Thereafter, a material having a relatively high carbon or carbide content may be sprayed onto the sacrificial substrate. Afterwards, the sacrificial substrate material may be removed. As a result, a medical implant component formed from only or substantially only the material having a relatively high carbon or carbide content may be formed.

In addition to spray techniques, and as previously described, a number of other processes may be utilized to form or in the formation of a medical implant component such as an injection molding technique, a cold isostatic press technique, or a press powder processing technique.

In an injection molding technique, the material having a relatively high carbon or carbide content may be used in an injection molding device so as to produce a medical implant component formed entirely or substantially entirely from such material. Alternatively, instead of just using the material having a relatively high carbon or carbide content, two or more materials may be utilized in the injection molding technique. For example, in a bi-material injection molding approach, two materials may be utilized such that a first material is initially injected and then a second material is injected. In such situation, the first material may be different from or the same as the second material. In a so-called double stroke arrangement, a first material (such as a biocompatible metal or material) may be injected in a first stroke so as to mold the desired component, and later a second material (such as the carbide material) may be feed or injected in a second stroke so as to overmold the component with the second material.

In a cold isostatic press technique, the material having a relatively high carbon or carbide content in powder form is used to create a so-called green density part of the medical implant. A binder may be utilized to compact this material. Such use of a binder may depend upon the morphology (i.e., a combination of shape and texture). Such green density part may have a density value which is less than that of the final part. For example, such green density part may have a density value of approximately 60-90% of the theoretical density of the powder. After the green density part is formed, it may be sintered, or sintered and hot isostatic pressed (HIP), or cold isostatic pressed and HIP. If a binder is used as mentioned above, such binder may be removed before sintering or HIPing. A furnace may be used to de-bind and sinter.

In a press powder processing technique, a mechanical press and a dye having the desired shape may be utilized to form the desired component. Here, the desired material in powder form may be fed into the dye and afterwards, a piston may press the material into the shape of the desired component (green density). Thereafter, the component may be sintered, and afterwards, may be subjected to a HIPing process.

By utilizing a material having a relatively high carbon or carbide content which may be formed by use of one of the techniques described above to coat a desired surface of a medical implant component or to form a medical implant component, provides a medical implant component which has exception wear properties.

Several examples of the present invention will now be described.

Initially, a brief description of some parameters and/or conditions will be provided. Weight percentage is utilized, unless otherwise indicated as vol % (volume fraction). Because the density of Cr23C6 is almost the same as CoMoCr metallic alloy, the weight percentage is close to volume percentage. For the following description, assume that all the carbon is in the form Cr23C6 in chrome carbide/CoCrMo alloy, and all the chromium is formed into carbide phase of Cr23C6 and metallic phase of pure Cr or CoCrMo alloy. This may have a linear relationship between carbon content and carbide content.

Compared to the previously described typically used material, that is F75 CoCrMo alloy which may have a carbon content of approximately 0.28-0.35 wt %, the present invention may have a material composition carbon content of approximately 0.36-13.33 wt % (carbide content of approximately 6.17-100 wt %). In this range, the composition may be divided into two zones. Zone 1 may have Cr23C6 phase and free chromium (Cr) or chromium alloy phase (CoCrMo alloy). Zone 2 may have a single phase of Cr23C6, Cr7C3, or Cr3C2 or a combined two or three carbides phases from among Cr23C6, Cr7C3, or Cr3C2.

The first example has a carbide phase of Cr23C6 and metallic phase of CoCrMo metallic alloy. The carbide phase is distributed in metallic matrix. The Cr23C6 carbide concentration may be from approximately 6.17 wt % to 32.05 wt %, while the CoCrMo metal is correspondingly from 93.83 wt % to 67.95 wt %. The primary elements (>1.0 wt %) are Cr, C, Co, Mo and other minor elements less than 1.0 wt %. The chemical composition ranges C 0.36-1.84 wt %, Cr 28.32-54.20 wt %, Co 39.30-65.00 wt %, Mo 4.1-6.0 wt %, Si 0.25-0.96 wt %, other trace elements <1.0 wt %. This composition of material may provide a hardness for the implant surface of approximately 400-730 HV at 300 g load at a density of about 98%. This material may provide better hardness as compared to the standard F75 alloy 400 HV at 300 g load condition.

The second example may have a carbide phase of Cr23C6 and metallic phase of CoCrMo metallic alloy. The carbide phase is distributed in metallic matrix. The Cr23C6 carbide concentration may be from approximately 32.06 wt % to 65.16 wt %, while the CoCrMo metal is correspondingly from 67.94 wt % to 34.84 wt %. The primary elements (>1.0 wt %) are Cr, C, Co, Mo and other minor elements less than 1.0 wt %. The chemical composition ranges C 1.85-3.70 wt %, Cr 54.20-73.10 wt %, Co 20-39.30 wt %, Mo 2.0-4.0 wt %, Si 0.14-0.25 wt %, other trace elements <1.0 wt %. This composition of material may provide a hardness for the implant surface of approximately 730-970 HV at 300 g load at a density of about 98%. This material may provide improved hardness as compared to that obtained in the first example or the standard F75 alloy.

The third example may have a carbide phase of Cr23C6 and metallic phase of CoCrMo metallic alloy. The carbide phase is distributed in metallic matrix. The Cr23C6 carbide concentration may be from approximately 65.16 wt % to 99.99 wt %, while the CoCrMo metal is correspondingly from 34.84-0.01 wt %. The primary elements (>1.0 wt %) are Cr, C, Co, Mo and other minor elements less than 1.0 wt %. The chemical composition ranges C 3.70-5.67 wt %, Cr 0.73.10-99.00 wt %, Co 0-20.00 wt %, Mo 0-2.0 wt %, Si 0-0.14 wt %, other trace elements <1.0 wt %. This composition of material may provide a hardness for the implant surface of approximately 970-1200 HV at 300 g load at a density of about 98%. This material may provide improved hardness as compared to that obtained from the first example, the second example or the standard F75 alloy.

The fourth example may have a carbide phase of Cr23C6 and metallic chromium phase. The carbide phase is distributed in metallic matrix. The Cr23C6 carbide concentration may be from approximately 6.17 wt % to 99.99 wt %, while the Cr metal is correspondingly from 93.83 wt % to 0.01 wt %. The primary elements (>1.0 wt %) are Cr and C, other minor elements less than 1.0 wt %. The chemical composition ranges C 0.36-5.68 wt %, Cr 94.32-99.64 wt %. This material may provide a hardness of approximately 400-1200 HV at 300 g load at a density about 98%. Accordingly, as compared to that obtained from the standard F75 alloy or any of the first, second and third examples, this material may provide improved hardness and/or corrosion resistance. Additionally, this material may provide a relatively small coefficient of thermal expansion (CTE) to match a relatively low CTE substrate such as Ti6Al4v alloy. Further, cobalt ions may not be released from this material in the body.

The fifth example may have pure Cr23C6 phase without any metal. The primary elements (>1.0 wt %) are Cr and C, other minor elements less than 1.0 wt %. The chemical composition is C 5.68 wt %, Cr 94.32 wt %. This material may provide hardness of approximately 400-1200 HV at 300 g load at a density about 98%. Accordingly, as compared to that obtained from the standard F75 alloy or any of the first, second, third and fourth examples, this material may provide improved hardness and corrosion resistance. Additionally, this material may provide a relatively small coefficient of thermal expansion (CTE).

The sixth example may have pure Cr7C3 phase without any metal. The primary elements (>1.0 wt %) are Cr and C, other minor elements less than 1.0 wt %. The chemical composition is C 9.00 wt %, Cr 91.00 wt %. This material may have a hardness which is similar to or better than that of example five.

The seventh example may have pure Cr3C2 phase without any metal. The primary elements (>1.0 wt %) are Cr and C, other minor elements less than 1.0 wt %. The chemical composition is C 13.33 wt %, Cr 86.77 wt %. This material may have the highest hardness as compared to the previous six examples and F75 alloy.

Although in the above description of the above embodiments the carbon or carbide source may have been indicated to be graphite and the biocompatible material may have been indicated to be cobalt chrome or an alloy thereof, the present invention is not so limited. Instead, other materials may be used for the carbon or carbide source and for the biocompatible material.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of fabricating a medical implant component, said method comprising:

producing a substrate from a first material, said substrate having a bearing portion; and spraying particles of a second material using a thermal type spraying process onto at least the bearing portion of the substrate, said second material being formed from a biocompatible material and a carbide, in which the carbide content is 6.17% or more of the second material by weight, the carbide is a chrome carbide, the chrome carbide is in the form of $Cr_{23}C_6$, an average size of a particle of the carbide has a size of approximately 900 nm or less, and the biocompatible material is cobalt chrome, titanium, a titanium alloy, zirconium, a zirconium alloy, stainless steel, or a cobalt based super alloy, wherein upon completion of the fabrication, the bearing portion is a bearing surface which is operable to articulate with a portion of a bone or another medical implant component.

2. The method according to claim 1, in which the size of said particle of the carbide in the second material is within a range of approximately 10-200 nm.

3. The method according to claim 1, in which the first material is the same as the second material.

4. The method according to claim 1, in which the first material is different from the second material.

5. The method according to claim 1, in which the carbide source is graphite.

6. The method according to claim 1, wherein said thermal type spraying process is a plasma spraying process or a high velocity oxygen fuel spraying process.

7. The method according to claim 6, wherein the high velocity oxygen fuel spraying process is a gas fuel process or a liquid fuel process.

8. The method according to claim 7, wherein the gas fuel process is a propane type process and the liquid fuel process is a kerosene type process.

9. A method of fabricating a medical implant component, said method comprising:

producing a sacrificial substrate representative of the medical implant component from a first material;

spraying particles of a second material using a thermal type spraying process onto the sacrificial substrate, said second material being formed from a biocompatible material and a carbide, in which the carbide content is 6.17% or more of the second material by weight, the carbide source is a chrome carbide, the chrome carbide is in the form of $Cr_{23}C_6$, a particle of the carbide source has a size of approximately 900 nm or less, and the biocompatible material is cobalt chrome, titanium, a titanium alloy, zirconium, a zirconium alloy, stainless steel, or a cobalt based super alloy; and removing the sacrificial substrate.

10. The method according to claim 9, in which the size of said particle of the carbide source in the second material is within a range of approximately 10-200 nm.

11. The method according to claim 9, in which the first material is an easily dissolvable or meltable material.

12. A method of fabricating a medical implant component, said method comprising:

producing a sacrificial substrate representative of the medical implant component from a first material, in which the first material is salt;

spraying particles of a second material onto the sacrificial substrate using a thermal type spraying process, said second material being formed from a biocompatible material and a carbide, in which the carbide content is 6.17% or more of the second material by weight; and removing the sacrificial substrate.

13. The method according to claim 9, in which the carbide source is graphite.

14. The method according to claim 9, wherein said thermal type spraying process is a plasma spraying process or a high velocity oxygen fuel spraying process.

15. The method according to claim 14, wherein the high velocity oxygen fuel spraying process is a gas fuel process or a liquid fuel process.

16. The method according to claim 15, wherein the gas fuel process is a propane type process and the liquid fuel process is a kerosene type process.

* * * * *